US012788419B2

(12) United States Patent
Funder et al.

(10) Patent No.: US 12,788,419 B2
(45) Date of Patent: Nov. 10, 2026

(54) LITHOTRIPSY DEVICE, LITHOTRIPSY SYSTEM AND METHOD FOR OPERATING A LITHOTRIPSY DEVICE

(71) Applicant: KARL STORZ SE & CO. KG, Tuttlingen (DE)

(72) Inventors: Marius Funder, Tuttlingen (DE); Bernhard Glöggler, Tuttlingen (DE); Thomas Hinding, Tuttlingen (DE); Florian Huber, Tuttlingen (DE); Beat Krattiger, Tuttlingen (DE)

(73) Assignee: KARL STORZ S.E. & Co. KG, Tuttlingen (DE)

( * ) Notice: Subject to any disclaimer, the term of this patent is extended or adjusted under 35 U.S.C. 154(b) by 598 days.

(21) Appl. No.: 18/258,732

(22) PCT Filed: Dec. 20, 2021

(86) PCT No.: PCT/EP2021/086873
§ 371 (c)(1),
(2) Date: Jun. 21, 2023

(87) PCT Pub. No.: WO2022/136311
PCT Pub. Date: Jun. 30, 2022

(65) Prior Publication Data
US 2024/0050112 A1 Feb. 15, 2024

(30) Foreign Application Priority Data
Dec. 22, 2020 (DE) ..................... 10 2020 134 602.6

(51) Int. Cl.
*A61B 17/22* (2006.01)
*A61B 17/32* (2006.01)

(52) U.S. Cl.
CPC .................. *A61B 17/22012* (2013.01); *A61B 17/320068* (2013.01); *A61B 2017/22011* (2013.01);
(Continued)

(58) Field of Classification Search
CPC ...... A61B 17/22012; A61B 17/320068; A61B 2017/22011; A61B 2017/22014;
(Continued)

(56) References Cited

U.S. PATENT DOCUMENTS

| | | | |
|---|---|---|---|
| 3,830,240 | A | 8/1974 | Antonevich et al. |
| 9,421,023 | B2 | 8/2016 | Bond et al. |

(Continued)

FOREIGN PATENT DOCUMENTS

| | | | |
|---|---|---|---|
| CN | 105556590 | A | 5/2016 |
| CN | 111655178 | A | 9/2020 |

(Continued)

OTHER PUBLICATIONS

Intellectual Property India, Examination Report, Application No. 202327041501, dated Oct. 24, 2025.

(Continued)

*Primary Examiner* — Robert A Lynch
(74) *Attorney, Agent, or Firm* — Brooks Kushman P.C.

(57) ABSTRACT

The disclosure relates to a lithotripsy device comprising an elongate probe, which can be inserted into a body interior of a human or animal body, and a drive arrangement for deflecting the probe, which is arranged at a proximal portion of the probe, the drive arrangement comprising an ultrasonic converter unit for exciting ultrasonic vibrations in the direction of a longitudinal extension of the probe, and the drive arrangement having a deflection device for exerting a time-varying force onto the probe in a direction transversely to the longitudinal extension of the probe. The disclosure also relates to a lithotripsy system and to a method for operating a lithotripsy device.

18 Claims, 8 Drawing Sheets

(52) U.S. Cl.
CPC ............... *A61B 2017/22014* (2013.01); *A61B 2017/320098* (2017.08); *A61B 2503/00* (2013.01)

(58) Field of Classification Search
CPC ......... A61B 2017/22015; A61B 2017/320071; A61B 2017/320072; A61B 2017/320073; A61B 2017/320098; B06B 3/00; B06B 3/02; B06B 1/00; B06B 1/0611; B06B 1/12; B06B 1/16; B06B 1/161; B06B 1/162; B06B 1/167; B06B 1/168
See application file for complete search history.

(56) References Cited

U.S. PATENT DOCUMENTS

| | | | | |
|---|---|---|---|---|
| 2004/0010267 | A1 | 1/2004 | Nakamura et al. | |
| 2005/0021065 | A1* | 1/2005 | Yamada ........... | A61B 17/32002 606/169 |
| 2014/0371636 | A1* | 12/2014 | Bond ............... | A61B 17/22012 601/2 |

FOREIGN PATENT DOCUMENTS

| | | | |
|---|---|---|---|
| DE | 2053982 | A1 | 5/1972 |
| DE | 3826414 | A1 | 2/1989 |
| EP | 0421285 | A1 | 4/1991 |
| WO | 2019/141822 | A1 | 7/2019 |

OTHER PUBLICATIONS

The International Bureau of WIPO, International Preliminary Report on Patentability, Application No. PCT/EP2021/086873, dated Jun. 13, 2023.
China Office Action, Application No. 2021800933473, dated May 24, 2024.
European Patent Office, International Search Report and Written Opinion, Application No. PCT/EP2021/086873, mailed Apr. 8, 2022. ISA/European Patent Office.

* cited by examiner

LITHOTRIPSY DEVICE, LITHOTRIPSY SYSTEM AND METHOD FOR OPERATING A LITHOTRIPSY DEVICE

CROSS-REFERENCE TO RELATED APPLICATIONS

This application is the U.S. national stage of PCT/EP2021/086873 filed on Dec. 20, 2021, which claims priority of German Patent Application No. DE 10 2020 134 602.6 filed on Dec. 22, 2020, the contents of which are incorporated herein.

TECHNICAL FIELD

The present disclosure relates to a lithotripsy device, in particular a device for intracorporeal lithotripsy by means of ultrasonic vibrations, and also to a lithotripsy system and a method for operating a lithotripsy device.

BACKGROUND

In order to remove a stone from inside the body, for example from the urinary tract, it is often necessary to first break up the stone so that the resulting fragments can be easily removed. For this purpose, it is known, for example, to guide a probe toward the stone and to excite the probe to perform longitudinal ultrasonic vibrations (i.e. ultrasonic vibrations oriented in the longitudinal direction) which, when the probe comes into contact with the stone, cause fragments to break off, in order thereby to ablate or crush the stone. However, it has been shown that the ablation or crushing action of the probe is not sufficient in all applications if it only acts on the stone with longitudinal ultrasonic vibrations.

According to DE 20 53 982, a device for rendering cystic, urethral and renal calculi harmless is provided with a curved snout which is connected to a power converter and by which the axial vibrations of the probe are in part converted into flexural vibrations. The document U.S. Pat. No. 3,830,240 discloses that an ultrasonic transducer is connected to a catheter via a coupling part, wherein a longitudinal movement is converted into a transverse movement by means of a laterally arranged screw or a lateral insertion of the catheter into the coupling part. According to DE 38 26 414 A1, an ultrasonic therapy device has an ultrasonic vibrator for generating ultrasonic vibrations in the axial direction of the device and in a direction different than the axial direction, wherein piezoelectric elements of the ultrasonic vibrator have a non-uniform thickness or pretensioning.

The device described in EP 0 421 285 A1 for crushing concretions located in body cavities consists of at least one piezoelectric transducer element between a reflector and a horn, wherein ultrasonic waves are directed to the concretions from the horn by means of a sonotrode. In order to generate transverse and rotational vibrations, the horn is provided on its surface with depressions that run non-parallel to its axis of symmetry.

A device for crushing a stone in the body is known from WO 2019/141822 A1, which device comprises a probe and a drive unit for deflecting the probe or for introducing a shock pulse into the probe along its longitudinal extent, wherein the drive unit has a first drive device for periodically deflecting the probe and a second drive device for pulsed deflection of the probe. The first drive device acts on the probe via a vibrating part. The second drive device comprises an electromagnet, which accelerates a projectile along a longitudinal axis onto an impact body which transmits the impact impulse onto a collar element of the probe. The periodic and the pulsed deflection can be superimposed.

According to U.S. Pat. No. 9,421,023 B2, a device for transmitting ultrasonic vibrations comprises a horn, which receives vibrations from an actuator, and an ultrasonic waveguide which is firmly coupled to the horn and on which a stop and two shock-pulsing masses, each with a circular cross section, are arranged. The shock-pulsing masses are mounted movably on the ultrasonic waveguide. Such an impact of a shock-pulsing mass on the stop, in which a side region of the shock-pulsing mass strikes the edge of the stop, causes low-frequency shock pulses that travel both longitudinally and transversely along the central axis of the ultrasonic waveguide and result in a simultaneously longitudinal and transverse deflection of the distal end of the waveguide tube.

The devices mentioned are not always satisfactory in terms of the ablation or crushing effect. In particular, in the treatment of a stone in the body, the effect of the probe may diminish after some time or may come to a virtual stop, thereby prolonging the operating time, and/or the stone may escape from the operating field, requiring the probe to be relocated and realigned, which may likewise result in the operating time being extended. Furthermore, some of the devices mentioned have a high level of complexity and are not optimal in terms of cleaning and sterilization.

It is an object of the present disclosure to improve on the prior art. In particular, it is an object of the present disclosure to make available a lithotripsy device, a lithotripsy system and a method for operating a lithotripsy device, the above-mentioned disadvantages being avoided as far as possible and, in particular, an improved effectiveness and thus a reduced operating time and/or a simpler construction being achievable.

SUMMARY

This object is achieved by a lithotripsy device, a lithotripsy system and a method for operating a lithotripsy device. Advantageous developments of the disclosure are set forth in the dependent claims.

The disclosure relates to a lithotripsy device, in particular a device for intracorporeal lithotripsy using ultrasonic vibrations. A device according to the disclosure is designed to destroy concretions within a human or animal body, in particular to crush and/or ablate a stone from the body by means of a probe brought to the stone through a natural or artificial opening in the body. Examples of such stones are renal calculi, urinary calculi in the ureter, cystic calculi, gallstones or salivary calculi. By crushing or ablation of the stone, the latter can be broken up in such a way that the resulting fragments can be easily removed from the body, for example by flushing and suction. The device according to the disclosure can also be used for ablation and/or crushing of other concretions or solid objects inside or outside a body.

The lithotripsy device according to the disclosure comprises an elongate probe which is insertable into the interior of a human or animal body. The probe is designed in such a way that, during the use of the device, it can be inserted into the interior of the body and brought into contact with the stone in the body. The probe is designed to transmit ultrasonic vibrations and is preferably composed of a metallic material, for example stainless steel. In particular, the probe can be excited in order to transmit ultrasonic waves, for example in the form of standing waves. Depending on the application, the probe can be rigid, semi-rigid or flexible.

The probe is preferably rigid and dimensioned for insertion through the shaft of an endoscope, for example a nephroscope, which for this purpose can have a corresponding channel. The probe can be solid or can be designed as a hollow probe, with a hollow probe also enabling fragments of a stone treated with the probe to be suctioned off. Such a probe is in particular also referred to as a sonotrode.

A drive arrangement is arranged on a proximal portion of the probe, i.e. a portion near the user. The proximal portion can be a proximal end portion of the probe. The proximal portion of the probe is in particular a portion of the probe which, together with the drive arrangement, remains outside the body or outside the endoscope shaft when the probe is inserted into the interior of the body. The proximal portion of the probe can be, for example, about half the length or a quarter or a tenth of the length of the probe, or less, in each case measured from a proximal end of the probe. The drive arrangement is designed to deflect the probe, in particular to generate deflections of the probe from a resting state in the proximal portion of the probe, and the deflections can be transmitted through the probe to a distal end of the probe, i.e. an end remote from the user. The drive arrangement can be designed as a handpiece that can be held by a user when using the device.

The drive arrangement comprises an ultrasonic converter unit, which is arranged and designed to excite ultrasonic vibrations of the probe in the direction of a longitudinal extent of the probe. This direction, which is generally the direction of a longitudinal axis of the probe, is referred to below as the longitudinal direction; in the case where the probe is curved or flexible, the longitudinal direction is the direction of the longitudinal extent or of the longitudinal axis of the probe in its proximal portion. The ultrasonic converter unit is thus designed to excite longitudinal ultrasonic vibrations of the probe and is for this purpose connected to the probe. In particular, the ultrasonic converter unit can comprise an ultrasonic transducer for generating ultrasonic vibrations, and a coupling device, for example an ultrasonic horn, which is designed for coupling the ultrasonic vibrations, generated by the ultrasonic transducer, into the proximal portion of the probe. The probe is preferably connected firmly but detachably to the ultrasonic converter unit; for example, the probe can be screwed into a corresponding bore in the ultrasonic horn and can bear with a collar against a distal end of the ultrasonic horn. The ultrasonic vibrations generated by the ultrasonic transducer and coupled into the probe via the ultrasonic horn can be conveyed to a distal end of the probe and thus to a site of action located inside the body. Typically, the ultrasonic vibrations introduced into the probe by the ultrasonic converter unit have a frequency above about 15 kHz or above 18 kHz, for example in the range between 20 kHz and 30 kHz, with a longitudinal deflection of the distal end of the probe being able to attain a double (peak-to-peak) amplitude of, for example, 40 μm and more. The ultrasonic converter unit can additionally be designed to excite transverse ultrasonic vibrations of the probe.

According to the disclosure, the drive arrangement further comprises a deflection device for deflecting the probe by exerting a time-variable force on the probe in a direction transverse to the longitudinal extent of the probe. The direction transverse to the longitudinal extent of the probe, i.e. transverse to the longitudinal direction of the probe, is also referred to below as the transverse direction. The force is thus exerted in particular in a direction that lies in a plane perpendicular to a longitudinal axis of the probe, for example in a radial or tangential direction, relative to the longitudinal axis of the probe in the proximal portion. The force can be variable in terms of magnitude and/or direction. The time-variable force can in particular be a force exerted temporarily but repeatedly on the probe, the force being able to be exerted intermittently for example, or also constantly in terms of magnitude and direction over a limited period of time; however, the time-variable force can also be a force exerted on the probe continuously, but with a variable magnitude and/or variable direction, the term "continuously" also including, for example, a sinusoidally variable force that is temporarily zero.

The probe can be deflected in the proximal portion by the effect of the time-variable force in the transverse direction. The deflection device is thus designed and arranged in particular in such a way that the probe can be deflected transversely with respect to the longitudinal direction of the probe, which is also referred to below as lateral deflection. Preferably, the deflection device is arranged in such a way that the time-variable force can be applied to the probe at such a position, relative to the longitudinal direction of the probe, so as to maximize deflection in the transverse direction; for example, the force can be exerted on the probe at a predetermined or adjustable distance from a distal end of the ultrasonic converter unit. As a result, the probe can be excited in particular to perform vibrations in the transverse direction, i.e. lateral vibrations. The deflection of the probe or the vibrations excited in the proximal portion can be transmitted through the probe in the distal direction and cause a lateral deflection of the distal end of the probe. In this way, for example, it is possible to achieve a lateral deflection of the distal end in the range of about 20 to 300 μm (peak-to-peak). The deflection device can be connected permanently or detachably to the ultrasonic converter unit. The force from the deflection device can be exerted on the probe directly, in particular on a lateral surface of the probe, or indirectly.

The device can be connected to or comprise a control device for controlling the drive arrangement. The control device can be designed to control the ultrasonic converter unit to excite the longitudinal ultrasonic vibrations and to control the deflection device to deflect the probe by the action of a force on the probe in the direction transverse to the longitudinal extent of the probe and thus to generate the lateral deflection of the probe. The control device can be designed to operate the ultrasonic converter unit and the deflection device in a coordinated manner and/or independently of each other. In particular, the control device can comprise operating means for operation by the user of the device, so that the operator can control the device to excite the longitudinal ultrasonic vibrations and to deflect the probe in the transverse direction in a manner coordinated therewith, for example simultaneously, or also independently thereof.

Since the drive arrangement comprises a deflection device for deflecting the probe by the action of a variable force in a transverse direction on the probe, the probe can be excited to perform transverse movements, which lead to a transverse movement of the distal end. It has been observed that this can increase the ablation or fragmentation effect of the probe. It is assumed that the ablation or fragmentation effect of the probe is mainly due to the longitudinal ultrasonic vibrations of the probe. However, on account of the transverse movement, a point at which the probe acts on the stone in the body is changed and the effect of the ultrasonic vibrations can thereby be improved. For example, a stationary state, which can occur after some time when treating a stone solely with longitudinal ultrasonic vibrations and in which the ablation practically comes to a standstill, can be prevented or eliminated. In particular, continuous processing and rapid ablation or fragmentation of the stone can be achieved through a continuous but variable or temporarily recurring force on the probe in the transverse direction with simultaneous operation of the ultrasonic converter unit. Furthermore, by virtue of the fact that the drive arrangement comprises a deflection device for exerting on the probe, in the transverse direction, a variable force that can be controlled independently of the ultrasonic converter unit, the further advantage can be achieved that the generated transverse movement of the distal end of the probe can be controlled independently of the longitudinal ultrasonic vibrations of the probe and in particular is not firmly coupled to a movement of the probe in the longitudinal direction. As a result, the transverse movement can be optimally adapted to the requirements of the surgical situation and, for example, it is possible to prevent a situation where, on account of too strong a transverse movement, a stone escapes from an operating field observed with an endoscope and then has to be searched for and targeted again, which has the disadvantage of being time-consuming.

According to one embodiment of the disclosure, the deflection device is designed or can be controlled in such a way that a frequency and/or an intensity of the time-variable force that is exerted on the probe can be adjusted. In this context, "intensity" means in particular a magnitude or an amplitude of the force exerted or also the force impact, i.e. an impulse transfer to the probe caused by the time-variable force, or an impact strength when an impact is exerted on the probe. The adjustable frequency can be the frequency of a periodic change in the force exerted, for example in the case where the force is exerted on the probe continuously but with a periodically variable magnitude and/or a variable direction. If the deflection device is designed for temporary but repeatable exertion of the force on the probe in the transverse direction, the adjustable frequency can be a repetition frequency of the exertion of force. In particular, the frequency or the repetition frequency can be adaptable to a natural frequency of the ultrasonic transducer, the probe or the entirety of probe and ultrasonic transducer or ultrasonic converter unit, possibly including the stone in the body, and can be chosen, for example, approximately equal to such a natural frequency or deliberately unequal to the natural frequencies. For example, the frequency or repetition frequency can be adapted to a resonant frequency of the probe with regard to transverse or flexural vibrations. This resonant frequency can be the fundamental frequency of a flexural vibration of the probe, at which the length of the probe, measured between a connection of the probe to the ultrasonic converter unit, i.e. in particular the distal end of the ultrasonic horn, and the distal end of the probe is a quarter wavelength, or the frequency of corresponding harmonics. Preferably, the frequency or repetition frequency is in a low-frequency range in relation to the excitation frequency of the ultrasonic transducer, for example in a frequency range from 3 to 300 Hz, particularly preferably in a range from about 15 to about 35 Hz, or is adjustable in said frequency range. In particular, the control unit of the device can be designed for the user to set the repetition frequency. By virtue of the fact that a frequency or a repetition frequency of the exertion of the force on the probe is adjustable and, in particular, can be selected to be equal to or different than a natural frequency, a lateral deflection of the distal end of the probe can be maximized and/or the occurrence of a stationary state with a low ablation effect can be particularly reliably avoided. Since an intensity of the exertion of the force on the probe is adjustable, a lateral deflection of the distal end of the probe can be adapted to an operating situation, for example in order to avoid a situation where the stone that is being worked on moves out of the operating field.

Alternatively or additionally, a frequency of the time-variable force, in particular a repetition frequency of the temporary exertion of force in the transverse direction on the probe, can be fixed, for example equal to or different than one of the natural frequencies mentioned, in which case the control device can be preset accordingly, and/or an intensity of the time-variable force can be fixed. As a further alternative or in addition, the device or the control device can be designed for non-periodic repetition of the exertion of the force in the transverse direction on the probe, for example for triggering individual temporary force effects on the probe in a manner that can be controlled by the user.

According to one embodiment of the disclosure, the deflection device is designed to exert the time-variable force on the probe by an impact exerted on the probe in the proximal portion by means of at least one impact element; "impact" refers here in particular to a shock-like or impulse-like force that can be exerted directly or indirectly on the probe by a shock or impact. According to this embodiment, the time-variable force, which acts on the probe in the direction transverse to the longitudinal extent of the probe and effects a lateral deflection of the probe, is thus generated by an impact of the at least one impact element on a lateral surface of the probe in the proximal portion of the probe. The at least one impact element is arranged movably, for example mounted movably in the radial or tangential direction in relation to the longitudinal axis of the probe, so that it is movable for exerting the impact on the lateral surface of the probe. The lateral surface is, in particular, an approximately cylindrical surface that is symmetrical to a longitudinal axis of the probe, although it can also be a differently configured surface of the probe that is suitable for exerting an impact in the transverse direction. The at least one impact element is preferably movable in a plane perpendicular to the longitudinal axis of the probe or transverse to the longitudinal extent of the probe in the proximal portion. In particular, the deflection device is designed in such a way that repeated impacts can be exerted on the probe by means of the one or more impact elements. By virtue of the fact that the deflection device is designed to exert one impact or repeated impacts on a lateral surface in the proximal portion of the probe, a lateral deflection of the probe can be easily generated which causes a lateral deflection of the distal end of the probe. The impact generally excites the probe to perform lateral vibrations with the fundamental frequency and several upper frequencies. As a result, the effect for ablation or crushing of a stone can be further improved. Furthermore, a region of the surface of the probe in which the at least one impact element touches the surface of the probe during impact, and which is also referred to here as the "impact region", is preferably linear or planar, and the linear or planar extent of the impact region is determined in order to minimize wear of the probe.

Advantageously, the at least one impact element can be designed as a ram or hammer that is movable by means of a drive device in order to exert the impact the probe. The ram or hammer is mounted in particular so as to be movable in a radial direction, relative to a longitudinal axis of the probe, and can be driven by the drive device to strike a lateral surface of the probe on one side. In this way, a lateral deflection of the probe can be generated in a simple and reliable manner.

Advantageously, the at least one impact element can also be designed as a frame or as a slotted disk, which in each case is movable by means of a drive device, for exerting the impact on the probe on one side or alternating sides. The frame or the slotted disk can, for example, be guided displaceably in the transverse direction or can be mounted so as to be rotatable about a pivot axis which is approximately parallel to the longitudinal axis and spaced apart from the latter. According to this embodiment, the probe runs through the interior of the frame or through the slot in the disk, which is wider than a diameter of the probe. The end points of a reciprocating movement of the frame or of the slotted disk are such that the impact element, by movement in the transverse direction, can strike with a first inner side of the frame or of the slot against a first region of the lateral surface of the probe; more preferably, the impact element, by moving in the opposite direction, can strike with an opposite second side against a second region of the surface radially opposite the first region. As a result, it is possible to achieve a particularly efficient impact effect and, if the impact element exerts two opposite impacts on the probe during a full reciprocating movement, a higher impact frequency.

The frame or the slot of the disk can be closed on all sides or open on one side. A closed design has the advantage of increased stability and durability, while a frame open on one side or an open slot permits easier assembly and disassembly of the deflection device, without the probe having to be pulled longitudinally through the frame or the slot.

According to one embodiment of the disclosure, the drive device is designed as a linear drive, which drives the impact element in order to exert the impact on the probe. In particular, the drive device can be designed as a pneumatic drive comprising a pneumatic cylinder, as a linearly operating piezo motor or as an electromagnetic linear drive, for example with a magnetic coil and a displaceable iron core. Such a linear drive can act directly or indirectly, for example via a linkage, on the impact element. In particular, if the impact element is designed as a ram, hammer or movable frame, the linear drive can be arranged transverse to the longitudinal direction of the probe and can act directly on the impact element. This permits a particularly simple design of the deflection device, which can also makes cleaning and sterilization easier.

Alternatively, the drive device for driving the impact element can be designed, for example, in the manner of a hammer interrupter. This also permits a particularly simple configuration. In addition, a hammer interrupter can be operated without electronic control and can be designed without bearings that have to be lubricated and without corresponding seals, and the necessary electromagnet is able to be sealed off in a simple manner from the hammer or the probe. This can facilitate cleaning and sterilization.

According to a further embodiment, the drive device comprises a cam disk acting against a spring force. In this case, the impact element is guided displaceably, preferably in the radial direction, and is pretensioned by a spring against the cam disk. Upon rotation of the cam disk, the impact element performs a reciprocating movement. This embodiment is particularly advantageous in the case where the impact element is designed as a movable frame. Alternatively, the drive device can comprise a slider crank, which acts on the impact element and also sets the latter in a reciprocating movement. The cam disk or the slider crank can be driven in particular by an electric motor, a pneumatic motor, a rotary piezo motor or a turbine. Since the electric motor or the pneumatic motor, the piezo motor or the turbine acts on the probe via the cam disk or the slider crank and thus does not act directly on the probe, friction and resulting wear on the surface can be avoided. As a further alternative, the drive arrangement can comprise an electric motor which can be driven to perform a reciprocating movement and which is coupled to the impact element and can also set the latter in a reciprocating movement, preferably with an adjustable frequency. In this way too, a lateral deflection of the probe can also be easily achieved.

In the embodiments described above, the end points of the reciprocating movement are determined such that the impact element can strike against the surface of the probe. Furthermore, the intensity or strength of the impact, which is determined in particular by the speed, mass and material of the impact element, is selected in such a way that wear of the probe and repulsion of the treated stone in the body can be minimized and, at the same time, stone ablation can be maximized. The impact element is preferably made of a metallic or other hard material, for example stainless steel.

According to a further embodiment of the disclosure, the at least one impact element is designed as a mass body which, by means of a drive device, is movable on a circular path in order to exert the impact on the probe. For this purpose, the mass body can be arranged, for example, on a circumference of a rotatable disk that can be driven by the drive device, such that the mass body touches the lateral surface of the probe, when the circular movement is carried out, and the impact is thereby exerted on the probe. Preferably, the mass body is mounted with play or at least movable in a radial direction relative to an axis of rotation of the disk, so that, after the impact has been exerted through contact with the surface of the probe, the mass body can deviate during the further circular movement and can thereafter, by centrifugal force, return to a position of touching the probe during the subsequent rotation of the disk. In a particularly preferred manner, the mass body can be rotatably mounted on the disk, for example in the form of a ball bearing, the outer ring of which can strike against the probe and set it in rotation, thereby reducing friction and wear when touching the probe. As an alternative to a rotatable disk, the mass body can be held by a flexible holding means, such as a thread or a chain, on a rotatable shaft which can be driven by the drive device, and, as the shaft rotates, can be compelled by the centrifugal force onto a circular path in order to touch the lateral surface of the probe and thus exert the impact. The axis of rotation of the disk or shaft is preferably directed substantially parallel to the longitudinal direction of the probe, so that the at least one mass body is moved approximately tangentially, relative to the longitudinal axis of the probe, when the impact is exerted. The deflection device can also comprise a plurality of mass bodies which are arranged on the rotatable disk or held on the rotatable shaft, in order to exert repeated impacts on the probe. Since at least one mass body is provided which is movable on a circular path and thus touches the lateral surface of the probe in order to exert the impact, lateral deflections of the probe can be generated in a particularly simple and effective manner. The arrangement with play enables irregular excitations of the probe over a wide frequency range and good energy transmission from the disk or shaft to the probe.

The intensity of the time-variable force or the strength of the impact can be adjusted in an advantageous manner by a position of the axis of rotation and the radius of the disk or the length of the flexible holding means. The repetition frequency of the impacts is determined by the speed and the number of masses held on the disk or the shaft. The materials of the probe and the mass body can be designed for low wear; for example, the probe can be made of stainless steel and the mass bodies can be made of brass or of a slide-promoting plastic. In particular, for example, the disk can also be made of plastic and be designed in one piece with the mass bodies, for example in the manner of an impeller with elastic arms. In this way, it is possible to make available a particularly simple embodiment which, for example, can be intended for single use.

As an alternative or in addition to the force being exerted in the direction transverse to the longitudinal direction by an impact exerted on the surface of the probe, the deflection device can advantageously be designed to exert the force on the probe by means of an unbalanced drive, which can be driven by means of a drive device, or by an eccentric that can be driven by means of a drive device. This unbalanced or eccentric drive is coupled to the probe in the proximal portion thereof, so that the rotating unbalanced drive or the rotating eccentric can also exert a force on the probe in a direction transverse to the longitudinal direction. In this way too, a repeatable force can be easily exerted on the probe for the lateral deflection of the probe.

The drive device, which serves to move the mass body on a circular path or to drive the unbalanced or eccentric drive, can comprise an electric motor, a piezo motor, a pneumatic motor or also a turbine. Alternatively, an electric motor that can be driven in a reciprocating movement can be provided. In this way, the deflection device can be driven in a simple and reliable manner.

If, in the embodiments described within the scope of the present disclosure, the drive device comprises an electric motor, the latter is preferably a brushless electric motor, in particular with adjustable speed. A brushless electric motor has the particular advantages of high speeds, high power and a simple structure, which facilitates cleaning and sterilization. If the drive arrangement comprises a piezo motor, the latter can permit a particularly compact design and a large dynamic range. If the drive arrangement comprises a pneumatic motor, a pneumatic cylinder or a turbine, the particular advantage can thus be achieved that the deflection device can be operated without electrical lines; furthermore, operation with a vacuum or negative pressure may be possible, as a result of which increased security against contamination can be achieved.

The deflection device can comprise the above-described drive device, which can form a unit with the deflection device. However, it can also be provided that the drive device is arranged separately from the deflection device or is only partially comprised by it. In particular, it can be provided that a motor of the drive device, such as an electric motor, a piezo motor, a pneumatic motor or a turbine, which as mentioned above serves to drive the cam disk, the slider crank, the rotatable disk or shaft, for moving the mass body on a circular path, or the unbalanced or eccentric drive, is arranged separately from the deflection device and drives the latter via a flexible shaft. The flexible shaft can be permanently or detachably connected to the deflection device. In this way, the deflection device can be made particularly compact, and the handling of the device according to the disclosure can be improved.

According to one embodiment of the disclosure, the deflection device is arranged in such a way that the time-variable force acts on the probe, in the direction transverse to the longitudinal extent of the probe, distally with respect to the ultrasonic converter unit. In particular, the deflection device can be designed and arranged in order to exert the impact, exerted by means of the at least one movable impact element, on the lateral surface of a portion of the probe that lies distally with respect to the ultrasonic converter unit. This embodiment has the particular advantage that a distance between an impact region the impact and the ultrasonic converter unit can be adapted in such a way that a lateral deflection of the distal end of the probe is at a maximum. In particular, the deflection device can be connectable to the ultrasonic converter unit in such a way that the distance between the impact region of the impact and the ultrasonic converter unit is adjustable; this permits adaptation to different probes and/or different endoscopes, in order in each case to maximize the lateral deflection of the distal end of the probe.

Alternatively, it can be provided that the probe extends in the proximal direction beyond the ultrasonic converter unit and that the deflection device is arranged in such a way that the time-variable force in the direction transverse to the longitudinal extent of the probe acts on the probe proximally with respect to the ultrasonic converter unit or at least proximally with respect to a connection of the probe to the ultrasonic converter unit. In particular, the probe can extend through a bore in the ultrasonic converter unit, in which case the ultrasonic vibrations can be coupled into a collar of the probe, for example. The probe can be designed as a hollow probe, for example, and can be provided with a suction connection at its proximal end. In this way, a particularly compact and easy-to-handle configuration can be achieved; in particular, the deflection device can form a unit with the ultrasonic converter unit and, for example, can be integrated in a housing of the ultrasonic converter unit designed as a handpiece.

Further alternatively, the deflection device can be designed and arranged in such a way that, in order to exert the time-variable force on the probe in the direction transverse to the longitudinal extent of the probe, the deflection device exerts a force on the ultrasonic converter unit, as a result of which a time-variable force acts on the probe via the connection of the probe to the ultrasonic converter unit in order to deflect the probe laterally; for example, the force can be exerted on a distal end of the ultrasonic horn or on an attachment of the probe to the ultrasonic horn. This can be particularly advantageous in the case where the deflection device for exerting the force on the probe is designed in the form of an unbalanced or eccentric drive. A particularly compact configuration can also be achieved in this way.

According to one embodiment of the disclosure, the ultrasonic converter unit is mounted movably in a surrounding housing, it also being possible for the deflection device to be accommodated in the surrounding housing. The surrounding housing can be designed as a handpiece. In particular, the deflection device can be arranged to exert a force on the ultrasonic converter unit and can have a drive device designed as described above, for example a linear drive, a piezo motor, an electric motor with a slider crank, an unbalanced drive or an eccentric drive for generating a reciprocating movement of the ultrasonic converter unit in a transverse direction. In this case, the drive device can be supported against the surrounding housing, as a result of which a more efficient application of force to the ultrasonic converter unit and thus to the probe is made possible.

The ultrasonic converter unit can be mounted resiliently in the surrounding housing, in particular elastically, for example by means of a membrane. In this way, the surrounding housing can advantageously be mechanically decoupled from the lateral deflections generated by the deflection device, as a result of which handling can be further improved. The ultrasonic converter unit can be cardanically suspended in the surrounding housing by means of an intermediate ring, as a result of which a particularly extensive decoupling of the surrounding housing from vibrations is made possible.

Alternatively or in addition, the ultrasonic converter unit can be mounted in the surrounding housing so as to be pivotable about a transverse axis, the transverse axis being transverse to the longitudinal direction of the probe. In this case, it is particularly provided that, in order to exert the force on the probe in the direction transverse to the longitudinal extent of the probe, the deflection device exerts a force on the ultrasonic converter unit, as a result of which the ultrasonic converter unit is set in a pivoting movement and therefore the probe is deflected in the lateral direction. In order to generate a reciprocating pivoting movement of the ultrasonic converter unit, the deflection device can in particular comprise a linear drive, a piezo motor, an electric motor with a slider crank, an unbalanced drive or an eccentric drive. This embodiment can be designed to be particularly compact.

It can advantageously be provided that the ultrasonic converter unit and the deflection device are accommodated in the surrounding housing and that the surrounding housing is encapsulated or hermetically sealed. As a result, contamination, for example with a flushing liquid, can be avoided in a particularly reliable manner.

According to an advantageous embodiment of the disclosure, the drive arrangement is designed to exert a further force on the probe in a further direction transverse to the longitudinal extent of the probe. A force can thus be exerted on the probe in a number of different directions, each transverse to the longitudinal direction, for example in two directions perpendicular to each other. In particular, the drive arrangement can comprise a further deflection device, which is designed to exert a force on the probe in the further direction transverse to the longitudinal direction. For this purpose, the deflection devices can be offset relative to each other by a corresponding angle relative to a longitudinal axis of the probe, for example perpendicular to each other. As has been described above, the deflection devices can be identical to or different than one another and can be controlled, for example, simultaneously, alternately or independently of one another. A deflection of the probe in a further lateral direction can be brought about by the action of the force in the further transverse direction. A deflection of the probe can thus be generated in different directions, each transverse to the longitudinal direction, as a result of which the effectiveness for ablation or crushing of a stone in the body can be further increased.

According to a further aspect of the disclosure, a lithotripsy system, which is in particular a system for intracorporeal ultrasonic lithotripsy, comprises a lithotripsy device, which is designed as described above, and an endoscope, for example a nephroscope, which has a channel for inserting the probe into the interior of the human or animal body. The channel is dimensioned to allow the deflection of the probe, caused by the effect of the force in the direction transverse to the longitudinal extent of the probe, to be transmitted to a distal end of the probe. In particular, the probe, when inserted into the channel, has sufficient lateral play within the channel to convey a lateral deflection, which has been applied to the probe by the time-variable force exerted by the deflection device, as far as the distal end; if necessary, a seal can also be designed accordingly. A length of the channel is dimensioned such that the probe can be guided through the channel and extends beyond the distal end of the latter, so as to make contact with a stone located in front of the distal end. The advantages mentioned above can thus be achieved when treating the stone.

In a method according to the disclosure for operating a lithotripsy device which comprises an elongate probe, the probe is excited, in a proximal portion of the probe, to perform longitudinal ultrasonic vibrations, i.e. ultrasonic vibrations in the direction of a longitudinal extent of the probe, which are transmitted through the probe to a distal end of the probe. Furthermore, in the proximal portion, a time-variable force is exerted on the probe in a direction transverse to the longitudinal extent of the probe, in such a way that the probe is deflected transverse to its longitudinal direction, which deflection of the probe is transmitted through the probe to the distal end. In this way, the distal end of the probe can be set into longitudinal ultrasonic vibrations and at the same time can be deflected in the transverse direction, for example in the form of lateral vibrations.

Advantageously, it can be provided that the force is exerted repeatedly, in particular periodically repeatedly, on the probe in the transverse direction, it being possible for the repetition frequency to be adjustable. The force can be exerted on the probe continuously or intermittently. In order to deflect the probe, an impact can be exerted on a lateral surface of the probe by means of at least one impact element, for which purpose the impact element can be moved by means of a drive device. However, in order to deflect the probe, a force can also be exerted in the direction transverse to the longitudinal direction by means of an unbalance, which can be driven by means of a drive device, or an eccentric which can be driven by means of a drive device.

The lithotripsy device is preferably designed as has been described above. In particular, in order to excite the probe to perform the longitudinal ultrasonic vibrations, an ultrasonic converter unit can be provided, and, in order to exert the time-variable force in the transverse direction, a deflection device can be provided, in which case the probe, the ultrasonic converter unit and/or the deflection device are preferably designed and arranged as described above and operated as described above. The device according to the disclosure is designed in particular for carrying out the method.

The method according to the disclosure can be carried out extracorporeally and the lithotripsy device can be operated extracorporeally, in which case the probe is able to be brought with its distal end into contact with an object which can be worked on by the action of the ultrasonic vibrations and the lateral deflection of the probe.

However, the method according to the disclosure can also be carried out intracorporeally, in which case the probe is designed for introduction into the interior of a human or animal body. Before the method is carried out, the probe can be introduced, preferably through the shaft of an endoscope, into the interior of the body and advanced to a stone that is to be destroyed, so that the distal end of the probe touches said stone. When the method according to the disclosure is carried out, the stone is ablated or crushed. After the method has been carried out, flushing can take place in order to remove the fragments of the stone, and/or the probe can be removed from inside the body or from the endoscope shaft. The method can be carried out repeatedly.

In a method for intracorporeal lithotripsy using ultrasonic vibrations, the probe of a lithotripsy device configured as described above is inserted into the interior of a human or animal body and advanced to a stone that is to be destroyed, so that the distal end of the probe touches said stone, the lithotripsy device is operated as described above, and the stone is ablated or crushed, and, if necessary, the fragments can be removed by flushing, and the probe is removed from the interior of the body.

It will be appreciated that the aforementioned features and the features still to be explained below can be used not only in the respectively cited combination but also in other combinations or singly, without departing from the scope of the present disclosure.

BRIEF DESCRIPTION OF DRAWINGS

Further aspects of the disclosure will become clear from the following description of preferred exemplary embodiments and by reference to the appended schematic drawings, in which.

DETAILED DESCRIPTION OF PREFERRED EMBODIMENTS

Figure 1:
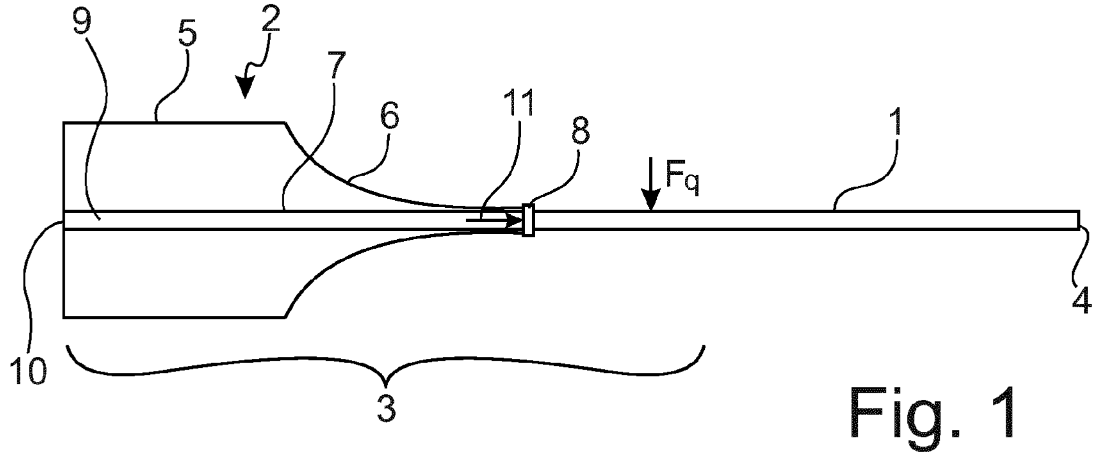
FIG. 1 shows a diagrammatic view of the mode of operation of a device according to the disclosure.

As is shown in FIG. 1 in the form of a simplified schematic diagram, a lithotripsy device comprises an elongate probe 1, which is also referred to as a sonotrode, and an ultrasonic converter unit 2, which is arranged on a proximal portion 3 of the probe 1. The probe 1 is designed for insertion into the interior of a human or animal body, such that a distal end 4 of the probe 1, also referred to as the probe tip, can be introduced through a natural or artificial body opening and advanced to a stone located inside the body. For this purpose, the probe 1 can be inserted into a corresponding channel of an endoscope passed through the body opening, for example through a nephroscope (not shown) to a kidney stone located in the renal pelvis. The proximal portion 3 of the probe 1 with the ultrasonic converter unit 2 remains outside the body and possibly also outside the endoscope. The probe 1 is preferably rigid, but may also be flexible or semi-rigid, and is typically made of stainless steel. The distal end 4 of the probe 1 can also have a movable crown.

The ultrasonic converter unit 2 comprises an ultrasonic transducer 5 which is coupled to a horn 6 in order to transmit ultrasonic vibrations. As a rule, the horn 6 is permanently connected to the ultrasonic transducer 5. The probe 1 is attached to a distal end of the horn 6. The probe 1 can, for example, be screwed into a through-bore 7 of the horn 6 so that a collar 8 of the probe 1 bears firmly on the distal end of the horn 6. The probe 1 can extend in the proximal direction through the ultrasonic transducer 5 or end in the region of the horn 6, for example. The horn 6 serves to amplify the ultrasonic vibrations generated by the ultrasonic transducer 5 and to couple the ultrasonic vibrations into the probe 1.

The coupled-in ultrasonic vibrations are transmitted as ultrasonic waves through the probe 1 to its distal end 4 and cause the latter to vibrate accordingly. As a rule, the ultrasonic transducer 5 is activated to generate standing waves in the probe 1, so that a vibration amplitude at the distal end 4 of the probe 1 is at a maximum. By placing the distal end 4 onto a stone in the body, these can lead to fragments breaking off or to the stone being made smaller. In this way, the stone can be gradually ablated or crushed.

It is indicated in FIG. 1 that the probe 1 can be designed as a hollow probe which has a continuous flushing channel 9. An attachment can be provided at a proximal end 10 of the ultrasonic transducer 5 or of the probe 1 for the purpose of attaching a flushing or suction device in order to remove the fragments of the stone that have formed. Alternatively, a flushing or suction connection can be provided on the side of the probe 1, distally with respect to the horn 6. By applying a negative pressure to the flushing channel 9, the stone can be sucked onto the distal end 4 of the probe 1, and shifting of the stone during treatment can thus be prevented.

As is shown symbolically in FIG. 1, the ultrasonic vibrations or ultrasonic waves generated by the ultrasonic transducer 5 and coupled into the probe 1 by the horn 6 are of a longitudinal nature, i.e. the corresponding deflection of the probe 1 takes place in the direction of the longitudinal extent of the probe. This longitudinal direction is indicated by the arrow 11. In addition, the generation of lateral ultrasonic waves by the ultrasonic converter unit 2 can also be provided.

According to the present disclosure, a time-variable transverse force $F_q$ acts on the probe 1 in a direction transverse to the longitudinal direction of the probe 1 and causes a lateral deflection of the probe 1. A deflection device is provided for this purpose and is arranged to exert the variable transverse force $F_q$ on the probe. For example, a flexural vibration of the probe 1 can be excited by a temporary, temporally recurring lateral force and is transmitted from the probe 1 to the distal end 4 of the latter. The distal end 4 of the probe 1 thus performs, in addition to the longitudinal ultrasonic vibrations, a lateral movement which is generally of low frequency. Such a lateral movement of the distal end 4 allows a considerable improvement in the ablation and/or fragmentation effect of the probe 1.

As is indicated in FIG. 1, the force $F_q$ can act on the probe 1 distally with respect to the ultrasonic converter unit 2, but still in the proximal portion 3 of the probe 1, which remains outside the body or the endoscope; alternatively, the force $F_q$ acting in the transverse direction can be exerted on the probe 1 within or proximally with respect to the ultrasonic converter unit 2 or indirectly via the latter. To exert the transverse force $F_q$ on the probe 1, a deflection device is provided which can be designed and arranged, for example, as in the exemplary embodiments explained below.

Figure 2A:
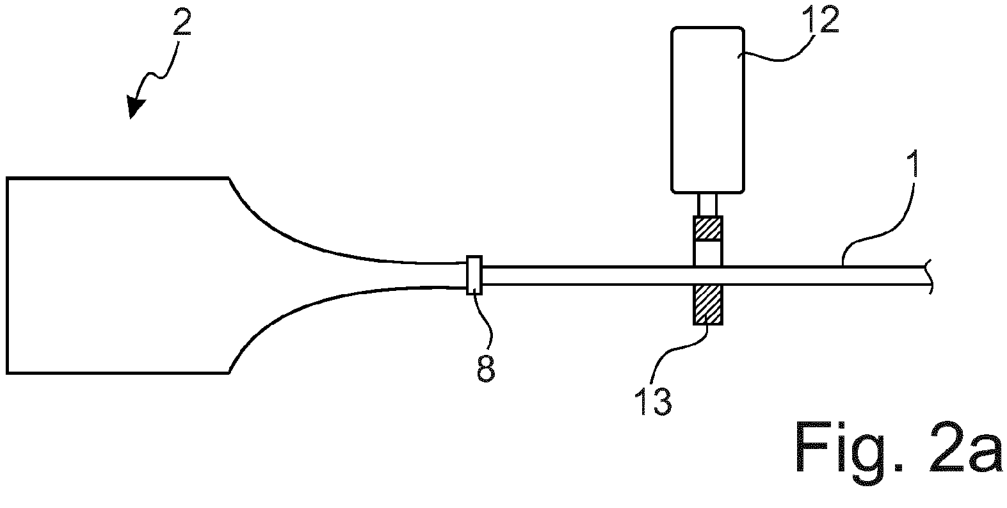
FIGS. 2*a* and 2*b* show a first exemplary embodiment of a device according to the disclosure.
Figure 2B:
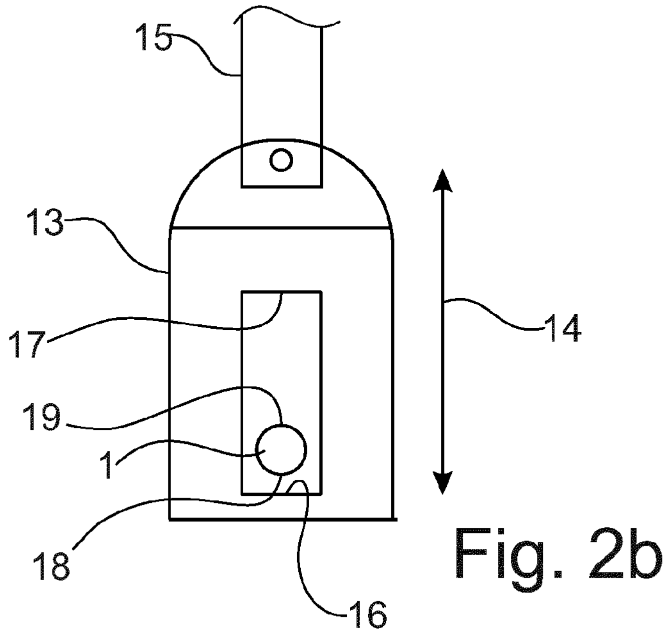

In the first embodiment of the device according to the disclosure, shown in a side view in FIG. 2*a*, the deflection device comprises a linear drive 12 which, for example, can be a pneumatic cylinder, a linearly operating piezo motor or an electromagnet with a displaceable iron core, which drive an impact element designed as a frame 13. As is shown in FIG. 2*b* in an axial view, the probe 1 runs through the interior of the frame 13. As is indicated by the double arrow 14, the frame 13 is guided in a direction transverse to the longitudinal extent of the probe 1 and is driven by the linear drive 12 to perform a reciprocating motion. The linear drive 12 acts on the frame 13 via a piston rod 15 or via a linkage, possibly with a certain amount of play. The end points of the reciprocating movement are determined such that the inner sides 16, 17 of the frame 13 alternately impact mutually opposite impact regions 18, 19 of the lateral surface of the probe 1; alternatively, the probe 1 can also be impacted on only one side. The frame 13 has a thickness in the longitudinal direction of the probe 1 such that the impact regions 18, 19, in which the frame comes into contact with the surface of the probe during impact, have a sufficient longitudinal extent to minimize wear on the surface of the probe 1 (see FIG. 2*a*). The deflection device with the linear drive 12 can comprise a holder, with which it is releasably attached (not shown) to the ultrasonic converter unit 2.

Figure 3:
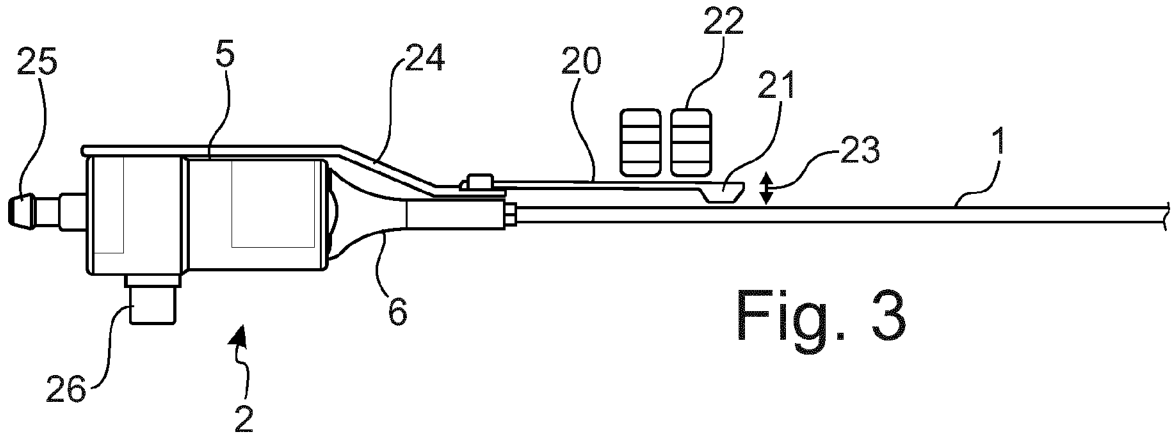
FIG. 3 shows a second exemplary embodiment of a device according to the disclosure.

According to the embodiment shown in a side view in FIG. 3, a deflection device with a drive device is provided for the lateral deflection of the probe 1 and works in the manner of a hammer interrupter. In this case, a hammer 21 is arranged on a leaf spring 20 and is driven by an electromagnet 22 with an armature and with an interrupter contact coupled thereto to perform a reciprocating movement in the transverse direction, which is indicated by the double arrow 23 in FIG. 3, and strikes the lateral surface of the probe 1. The leaf spring 20 can be attached to the ultrasonic converter unit 2 via a holding bracket 24.

FIG. 3 shows an example in which a hose attachment nozzle 25 is provided on the proximal side of the ultrasonic converter unit 2, for the purpose attaching a flushing and/or suction device, and is connected to a continuous flushing channel 9 of the probe 1 (see FIG. 1). The ultrasonic transducer 5 also has a supply connection 26 for electrical connection to a control device (not shown). The ultrasonic converter unit 2 of the other exemplary embodiments can be constructed in a corresponding manner.

Figure 4A:
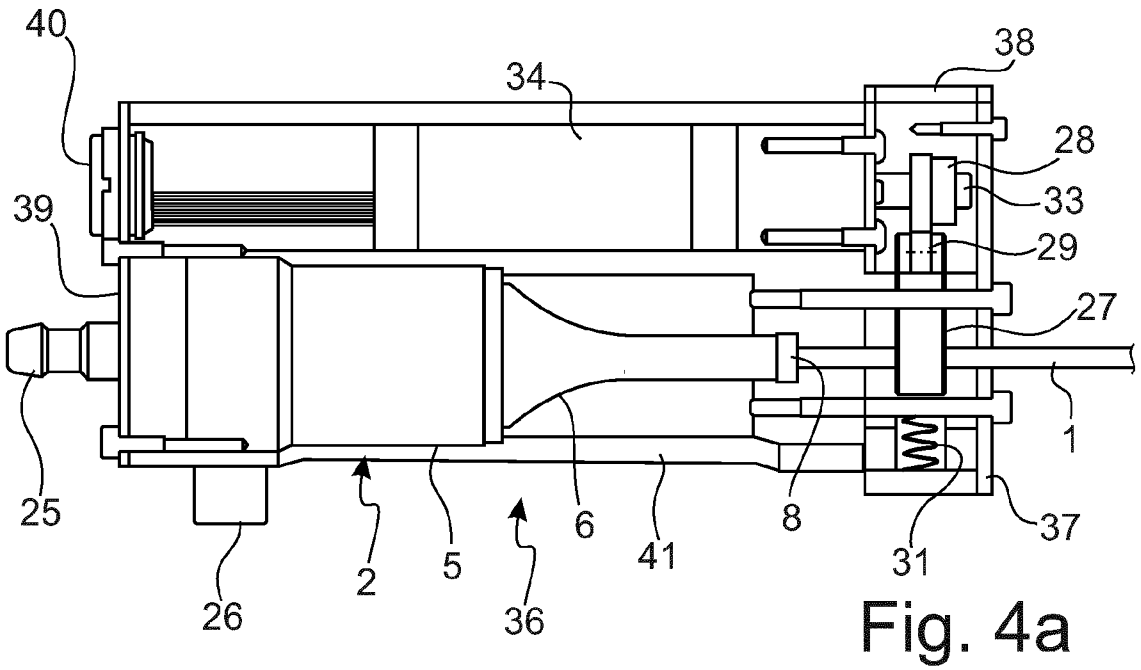
FIGS. 4*a* to 4*c* show a third exemplary embodiment of a device according to the disclosure.

FIG. 4*a* shows a third exemplary embodiment of a device according to the disclosure in a lateral and partially sectioned view. As in the first exemplary embodiment, the probe 1 is subjected to impacts acting on one or both sides by means of a frame 27 that is displaceable in the transverse direction, for which purpose the probe 1 runs through the frame 27 and a displacement path of the frame 27 is dimensioned in such a way that at least one of the inner sides 16, 17 of the frame 27 strikes against a corresponding impact region of the lateral surface of the probe 1 during the displacement. In the third exemplary embodiment, the deflection device further comprises a cam disk 28, which acts on a roller 29 mounted rotatably near an upper edge of the frame 27.

Figure 4B:
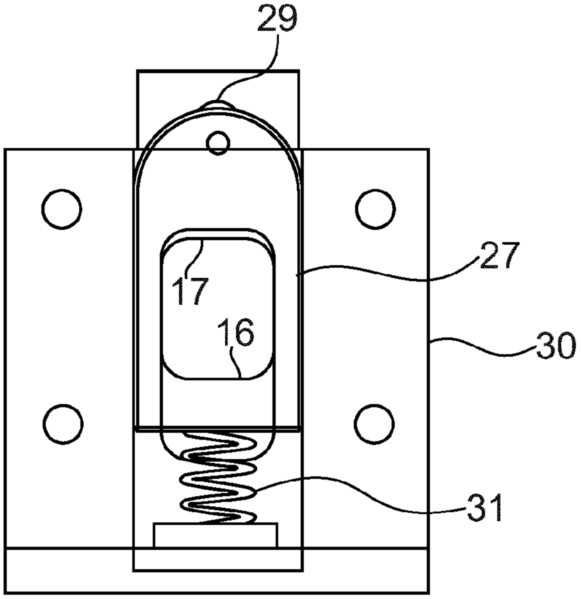
Figure 4C:
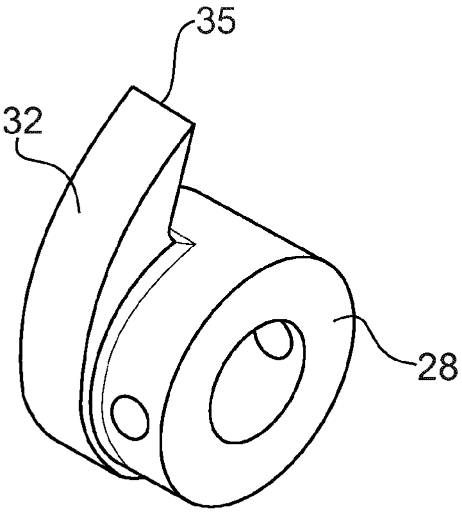

As is shown in an axial view in FIG. 4*b*, the frame 27 is mounted slidably in a guide unit 30. Here, the frame 27 is pretensioned by a spring 31 in the direction of the cam disk 28 (see FIG. 4*a*). The cam disk 28, which is shown in FIG. 4*c* in a view seen obliquely from the distal direction, has a control surface 32 over which the roller 29 rolls during rotation of the cam disk 28. The control surface 32 occupies an angular range of approximately 90° with respect to an axis of rotation of the cam disk 28; the roller 29 is not in contact with the cam disk 28 in a remaining angular range. The cam disk 28 is fastened to a motor shaft 33 of an electric motor 34, for example with a clamping screw, and can be set in rotation thereby.

When the cam disk 28 rotates clockwise, seen from the proximal direction, the roller 29 rolls along the control surface 32 in the direction of its tip 35, such that the frame 27 is displaced downward against the force of the spring 31. An end point of this movement can be determined such that an upper inner side 17 of the frame 27 strikes an upper surface of the probe 1. When the roller 29 resting on the control surface 32 exceeds the tip 35 thereof, the frame is pushed upward by the spring 31, with the lower inner side 16 of the frame striking a lower surface of the probe 1. By driving of the cam disk 28 by means of the electric motor 34, the frame 27 can be set in a reciprocating motion, with impacts being exerted on one or both sides of the probe 1 in the transverse direction, which impacts lead to a lateral deflection of the probe. The mass of the frame can be 16 g, for example, and the speed with which the lower inner side 16 of the frame 27 strikes the lower surface of the probe 1, can be for example 2.4 m/s or more, in order to achieve a sufficient impact effect for the lateral deflection of the probe.

FIG. 4*a* shows that the electric motor 34 and the ultrasonic converter unit 2 are arranged parallel to each other and are each firmly mounted in a surrounding housing 36. The surrounding housing 36 can be designed as a handpiece. The surrounding housing 36 comprises a closure plate 37 on the distal side, on which the guide unit 30 and a cover 38 of the cam disk 28 are held, and a closure plate 39 on the proximal side, through which protrude the hose attachment nozzle 25 and a connection socket 40 for connecting the electric motor 34 to a control device. The closure plates 37, 39 are screwed onto a body 41 of the surrounding housing 36. The relative position of the cam disk 28 and of the frame 29 in relation to the ultrasonic converter unit 2, relative to the longitudinal direction of the probe 1, defines an impact region of the probe 1 in which the force acting in the transverse direction acts on the probe 1. In the arrangement shown in FIG. 4*a*, the transverse force is exerted on the probe 1 distally with respect to the ultrasonic converter unit 2, at a distance of about 50 mm from the collar of the probe 1 or from the distal end of the horn 6.

Figure 5A:
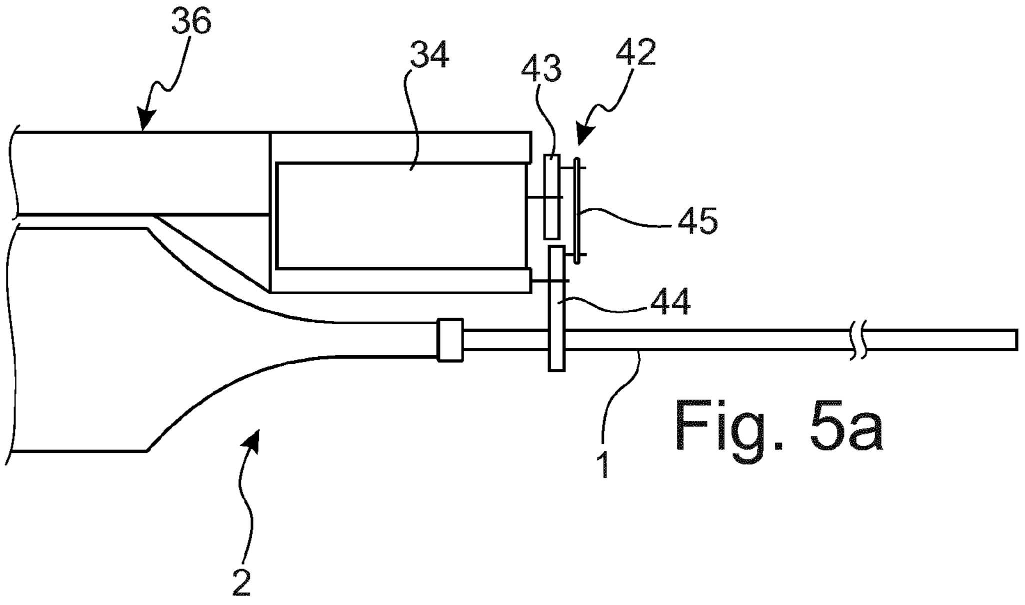
FIGS. 5*a* and 5*b* show a fourth exemplary embodiment of a device according to the disclosure.
Figure 5B:
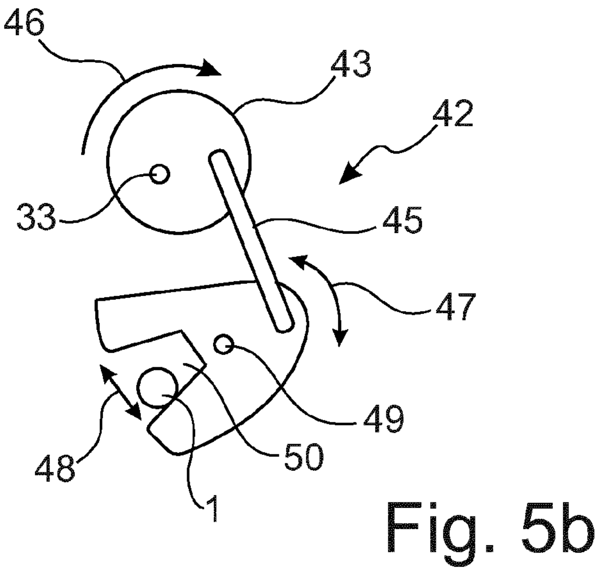

FIGS. 5*a* and 5*b* show a fourth embodiment of the device according to the disclosure in a lateral view and an axial view. As in the third exemplary embodiment, an electric motor 34 is provided here, which is mounted parallel to the ultrasonic converter unit 2 in a symbolically indicated surrounding housing 36. The electric motor 34 drives a slider crank mechanism 42 which comprises a drive disk 43, fastened to the motor shaft 33, and a slotted disk 44 which is mounted pivotably on the surrounding housing 36 and is connected to the drive disk 43 via a crank rod 45. As is indicated in FIG. 5*b*, a rotation (arrow 46) of the drive disk 43 is thereby converted into a reciprocating pivoting movement (double arrows 47, 48) of the slotted disk 44, with the axis 49 of the pivoting movement being directed parallel to the longitudinal extent of the probe 1. The starting point and end point of the pivoting movement are selected in such a way that the probe 1, which runs through the slot 50 of the slotted disk 44 (the slot being radial with respect to the axis 49), is subjected on one or both sides to a force from the walls of the slot 50, in particular an impact force. This can also cause a deflection of the probe 1 in the transverse direction.

Figure 6A:
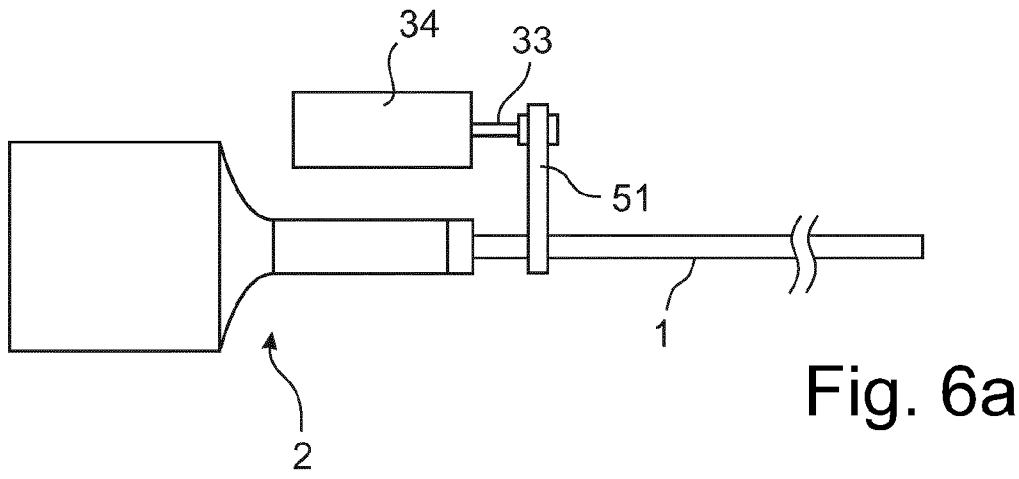
FIGS. 6*a* and 6*b* show a fifth exemplary embodiment of a device according to the disclosure.
Figure 6B:
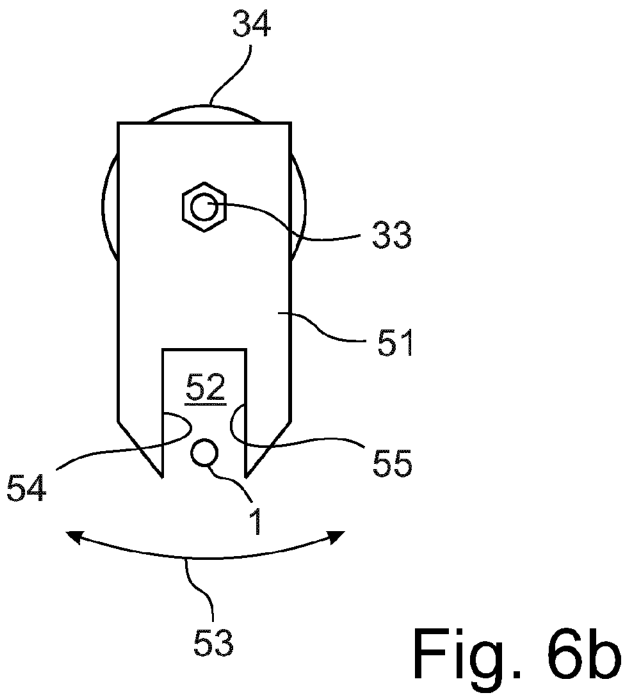

In the fifth embodiment shown in FIGS. 6*a* and 6*b* in a side view and an axial view, a coupling via a slider crank mechanism is replaced by a slotted disc 51 mounted on the motor shaft 33 of the electric motor 34. This is arranged in such a way that the probe 1 lies within the radial slot 52 of the slotted disk 51. The electric motor 34 is controlled in such a way, for example with a square-wave voltage, that the motor shaft 33 with the slotted disk 51 held on it executes a reciprocating movement (double arrow 53) in which the probe 1 is touched by one inner side or alternately by both inner sides 54, 55 of the walls of the slot 52. With this embodiment too, which can otherwise be configured like the fourth embodiment, the probe can be subjected to a force acting in the transverse direction and, given a corresponding design, in particular an impact effect.

Figure 7A:
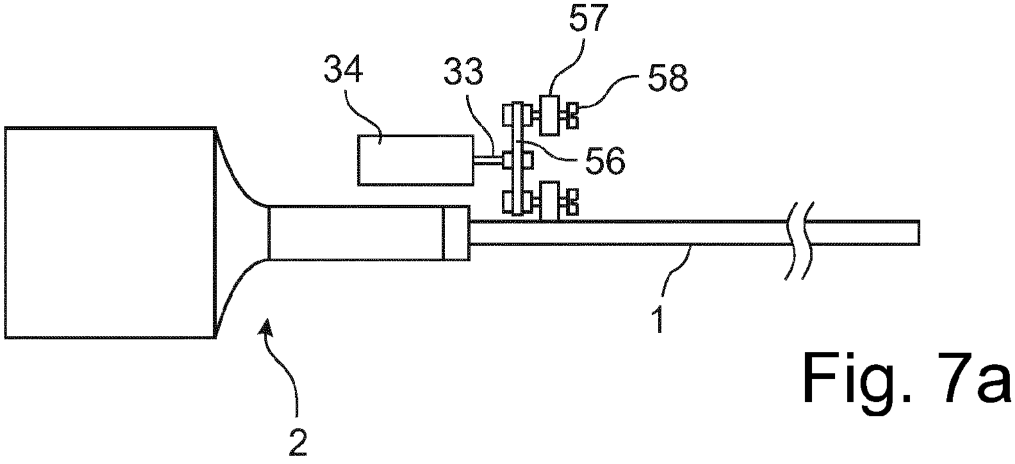
FIGS. 7*a* and 7*b* show a sixth exemplary embodiment of a device according to the disclosure.
Figure 7B:
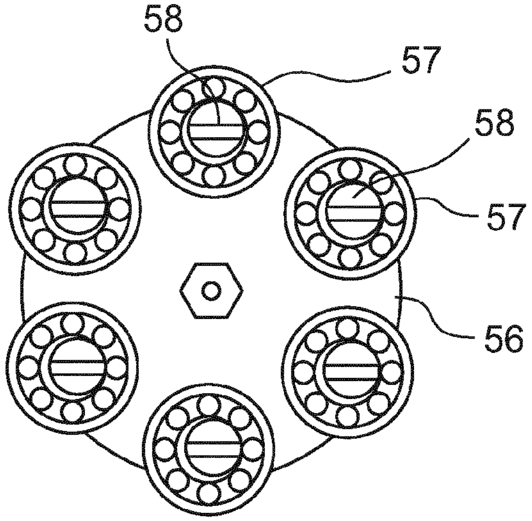

In the embodiment shown in FIGS. 7*a* and 7*b* in a side view and an axial view, an electric motor 34 with a motor shaft 33, which runs substantially parallel to the longitudinal direction of the probe 1, is arranged next to the ultrasonic converter unit 2 and can be connected to the latter in a manner similar to that explained in FIG. 4*a*. According to FIG. 7*a*, the deflection device comprises a drive disk 56 which is mounted on the motor shaft 33 of the electric motor 34 and near the circumference of which a plurality of impact bodies are arranged. In the example shown, these are six ball bearings 57, each of which is held with play on a bolt 58 which is directed parallel to the axis. Upon rotation of the drive disk 56, the outer rings of the ball bearings 57 strike the side of the probe 1 and thereby subject the probe 1 to a force directed transversely to the longitudinal extent of the probe 1, which is thereby excited to transverse vibration.

Figure 8:
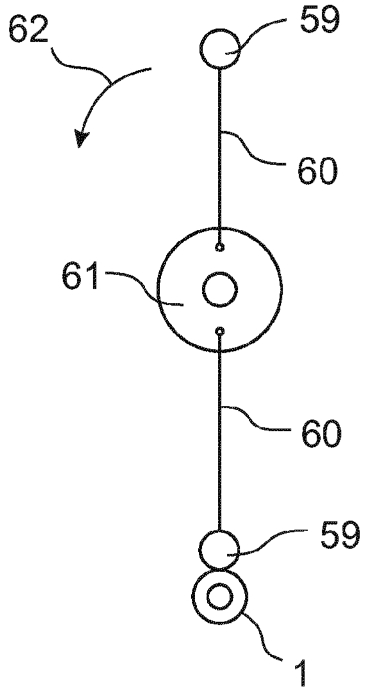
FIG. 8 shows a seventh exemplary embodiment of a device according to the disclosure.

According to FIG. 8, in a further embodiment that is otherwise designed as described above, impact masses 59 are each held on a rotatable drive disk 61 by means of a thread 60; instead of the thread 60, another flexible holding means, such as a chain, can also be provided. When the drive disk 61 is set in rotation by means of the electric motor, the impact masses 59 follow a circular path, as is indicated symbolically by the arrow 62. The path is routed in such a way that the impact masses 59 strike the surface of the probe 1 in the process.

Figure 9:
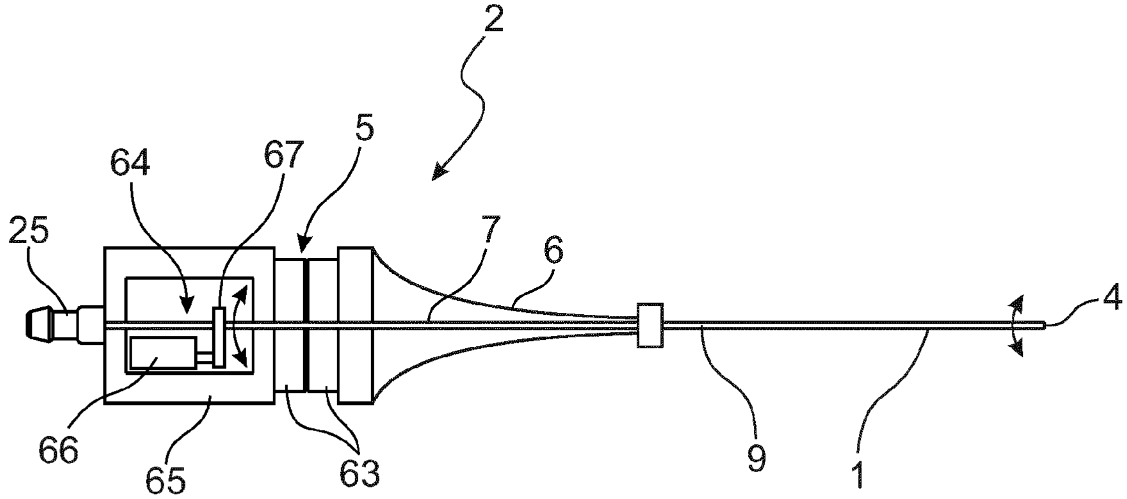
FIG. 9 shows an eighth exemplary embodiment of a device according to the disclosure.

In the exemplary embodiments described above, provision is made in each case that the time-variable force transverse to the longitudinal direction of the probe 1 acts on the probe 1 distally with respect to the ultrasonic converter unit 2. FIG. 9 shows an exemplary embodiment of the disclosure in a partially sectioned side view in which the time-variable force acting in the transverse direction acts on the probe 1 proximally with respect to the ultrasonic converter unit 2.

As is shown in FIG. 9, the ultrasonic converter unit 2 comprises an ultrasonic transducer 5 and a horn 6. The ultrasonic transducer 5 comprises a plurality of piezoelectric elements 63, stacked on one another in the longitudinal direction, for generating ultrasonic vibrations. The horn 6 and the ultrasonic transducer 5 have a through-bore 7 which is continuous in the longitudinal direction and through which the probe 1 is guided beyond the proximal end of the ultrasonic transducer 5.

A deflection device 64 is arranged proximally with respect to the ultrasonic transducer 5 and is accommodated in a housing 65 into which the probe 1 extends through a bore aligned with the through-bore 7 of the ultrasonic converter unit 2. In the embodiment shown in FIG. 9, the probe 1 has an axially continuous flushing channel 9 and is routed as far as a proximal side of the housing 65, where a hose connection nozzle 25 is arranged which communicates with the flushing channel 9.

An electric motor 66 is accommodated in an interior space of the housing 65, and a force acting in the transverse direction is exerted on the probe 1 by means of an eccentric disk 67, which can be set in reciprocating or continuous rotation by the electric motor 66 and thereby strikes against the probe 1. In principle, the deflection device 64 can instead be designed with a slotted disk or in accordance with another of the exemplary embodiments described above. The through-bore 7 is designed with sufficient clearance so that the deflections of the probe 1 generated in this way in the transverse direction can be transmitted through the ultrasonic converter unit 2 in the distal direction.

In this way, on the one hand, an impact can be exerted on the probe 1 in order to introduce a shock-like force, and, on the other hand, the rotating eccentric disk can also act as an unbalance or centrifugal mass which, via the electric motor 66 mounted in the housing 65, sets the unit formed by the deflection device 64 and the ultrasonic converter unit 2, and thus the proximal portion of the probe 1, in additional vibrations in the transverse direction, which generally represent lower frequency components compared to the impact excitation. These can likewise be transmitted to the distal end 4 of the probe 1 and deflect the latter in the transverse direction. The deflection device 64 and the ultrasonic converter unit 2 can be accommodated in a surrounding housing (not shown), which can be designed as a handpiece, and they can be mounted therein resiliently, for example.

Figure 10A:
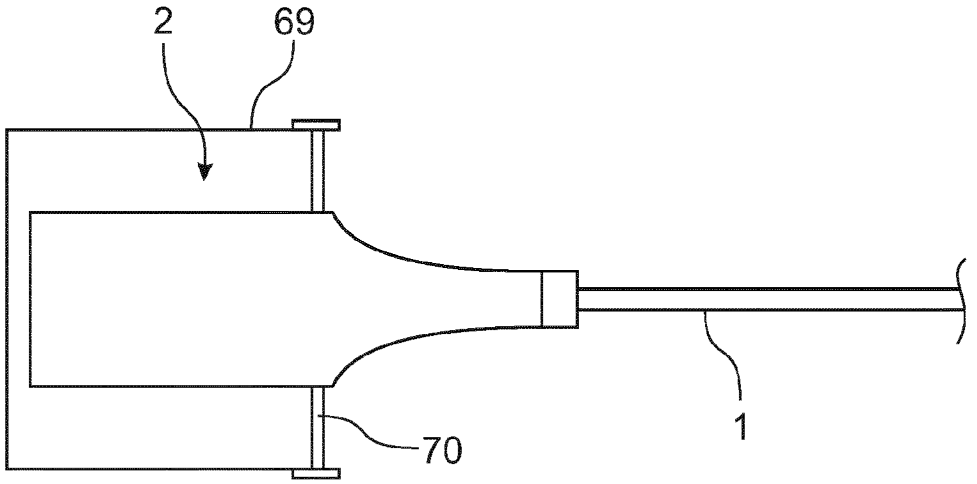
FIGS. 10*a* and 10*b* show a ninth exemplary embodiment of a device according to the disclosure.
Figure 10B:
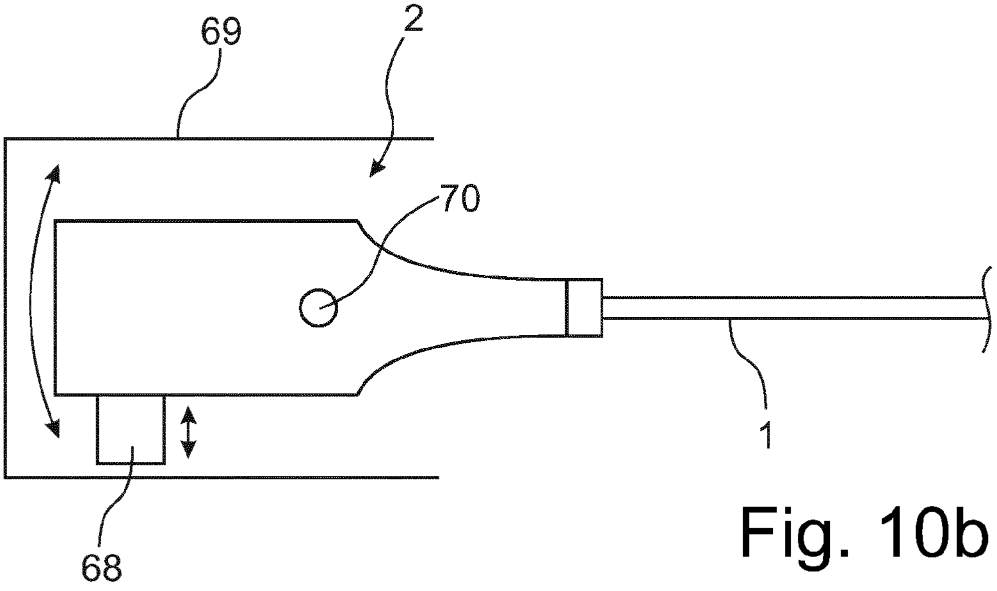

According to the ninth exemplary embodiment shown in FIGS. 10*a* and 10*b* in two side views rotated by 90° relative to each other, the ultrasonic converter unit 2 is moved, by a drive device 68 which acts between a surrounding housing 69 and the ultrasonic converter unit 2, in a reciprocating pivoting motion about an axis 70 which is transverse to the longitudinal axis of the probe 1 and which crosses through the ultrasonic converter unit 2 in a central portion. For this purpose, the drive device 68 can comprise, for example, a linear drive, such as a magnetic coil with a movable iron core, a piezo motor or an electric motor with a crank drive, as a result of which a time-variable transverse force is continuously exerted on the ultrasonic converter unit 2, in particular an alternating upward and downward force. Due to the pivoting movement of the ultrasonic converter unit 2 that is generated in this way, the probe 1 is deflected in the transverse direction in its proximal portion, as a result of which a lateral deflection of the distal end of the probe 1 can also be brought about.

In the above description, the terms "up" and "down" are to be understood only with reference to the representation in the figures; depending on the orientation of the device, a feature described in this way can also be oriented differently. The term "lateral" is used with reference to the longitudinal extent of the probe 1 and in particular denotes a lateral surface of a cylindrically designed probe 1.

For the sake of clarity, not all the reference signs are shown in all of the figures. Reference signs not explained in relation to a figure have the same meaning as in the other figures.

The invention claimed is:

1. A lithotripsy device, comprising:

an elongate probe which is insertable into the interior of a human or animal body;

an ultrasonic converter unit for exciting ultrasonic vibrations in the direction of a longitudinal extent of the probe;

a deflection device for exerting a time-variable force on the probe in a direction transverse to the longitudinal extent of the probe; and wherein the deflection device having an impact element configured to exert the time-variable force by exerting an impact onto a lateral surface of the probe independent of the operation of the ultrasonic converter unit.

2. The lithotripsy device as set forth in claim 1, wherein a frequency and/or an intensity of the time-variable force is adjustable.

3. The lithotripsy device as set forth in claim 1, wherein the impact element is a ram or hammer which is movable by means of a drive device in order to exert the impact on the probe.

4. The lithotripsy device as set forth in claim 3, wherein the drive device is designed as a linear drive or in the manner of a hammer interrupter.

5. The lithotripsy device as set forth in claim 3, wherein the drive device includes a cam disk acting against a spring force, or a slider crank which can be driven by an electric motor, a piezo motor, a pneumatic motor or a turbine, or comprises an electric motor which can be controlled to perform a reciprocating movement.

6. The lithotripsy device as set forth in claim 3, wherein a motor of the drive device is connected to the deflection device via a flexible shaft.

7. The lithotripsy device as set forth in claim 1, wherein the impact element is a frame which is movable by means of a drive device, or is a slotted disk which is movable by means of a drive device, in order to exert the impact on the probe.

8. The lithotripsy device as set forth in claim 1, wherein the impact element is a mass body which is movable by means of a drive device on a circular path in order to exert the impact on the probe.

9. The lithotripsy device as set forth in claim 8, wherein the drive device includes an electric motor, a piezo motor, a pneumatic motor, a turbine, or an electric motor which can be controlled to perform a reciprocating movement.

10. The lithotripsy device as set forth in claim 1, wherein the deflection device for exerting the time-variable force on the probe is an unbalanced form which can be driven by means of a drive device or in the form of an eccentric which can be driven by means of a drive device.

11. The lithotripsy device as set forth in claim 1, wherein the deflection device is arranged in such a way that the time-variable force acts on the probe, in the direction transverse to the longitudinal extent of the probe, distally with respect to the ultrasonic converter unit.

12. The lithotripsy device as set forth in claim 1, wherein the probe extends in the proximal direction beyond the ultrasonic converter unit, and in that the deflection device is arranged in such a way that the time-variable force acts on the probe, in the direction transverse to the longitudinal extent of the probe, proximally with respect to the ultrasonic converter unit.

13. The lithotripsy device as set forth in claim 1, wherein the deflection device is arranged to exert a force on the ultrasonic converter unit in order to exert the time-variable force on the probe in the direction transverse to the longitudinal extent of the probe.

14. The lithotripsy device as set forth in claim 1, wherein the ultrasonic converter unit is mounted movably in a surrounding housing.

15. The lithotripsy device as set forth in claim 14, wherein the ultrasonic converter unit is mounted resiliently in the surrounding housing and/or pivotably about a pivot axis transverse to the longitudinal extent of the probe.

16. The lithotripsy device as set forth in claim 1, wherein the drive arrangement is designed to exert a further time-variable force on the probe in a further direction transverse to the longitudinal extent of the probe.

17. A lithotripsy system comprising:

a lithotripsy device according to claim 1; and an endoscope having a channel for inserting the probe into the interior of the human or animal body, wherein the channel is dimensioned so as to allow a lateral deflection of the probe, effected by the time-variable force in the direction transverse to the longitudinal extent of the probe, to be transmitted to a distal end of the probe.

18. A method for operating a lithotripsy device comprising an elongate probe, wherein the probe, in a proximal portion, is excited to perform ultrasonic vibrations in the direction of a longitudinal extent of the probe, which ultrasonic vibrations are transmitted through the probe to a distal end of the probe, and, in the proximal portion, a time-variable force is exerted on the probe in a direction transverse to the longitudinal extent of the probe at a position different than a source of the ultrasonic vibrations, the time-variable force being independent of the ultrasonic vibrations, and a lateral deflection of the probe brought about thereby is transmitted through the probe to the distal end of the probe; and wherein the time-variable force is exerted by an impact exerted on a lateral surface of the probe.

* * * * *